(12) United States Patent
Jacobs et al.

(10) Patent No.: US 7,857,791 B2
(45) Date of Patent: Dec. 28, 2010

(54) MEDICATION DISPENSING APPARATUS WITH GEAR SET HAVING DRIVE MEMBER ACCOMMODATING OPENING

(75) Inventors: Alexander Thomas Jacobs, Cambridge, MA (US); Jared Alden Judson, Topsfield, MA (US)

(73) Assignee: Eli Lilly and Company, Indianapolis, IN (US)

( * ) Notice: Subject to any disclaimer, the term of this patent is extended or adjusted under 35 U.S.C. 154(b) by 1068 days.

(21) Appl. No.: 10/598,989

(22) PCT Filed: Mar. 25, 2005

(86) PCT No.: PCT/US2005/010205

§ 371 (c)(1),
(2), (4) Date: Sep. 18, 2006

(87) PCT Pub. No.: WO2005/097240

PCT Pub. Date: Oct. 20, 2005

(65) Prior Publication Data

US 2007/0191784 A1  Aug. 16, 2007

Related U.S. Application Data

(60) Provisional application No. 60/557,545, filed on Mar. 30, 2004.

(51) Int. Cl.
*A61M 5/315* (2006.01)
(52) U.S. Cl. .................................... 604/224
(58) Field of Classification Search ............. 604/224
See application file for complete search history.

(56) References Cited

U.S. PATENT DOCUMENTS

| 854,399 | A | 5/1907 | Bridge |
| 4,026,288 | A | 5/1977 | Costa et al. |
| 4,231,368 | A | 11/1980 | Becker |
| 4,300,554 | A | 11/1981 | Hessberg et al. |
| 4,465,478 | A | 8/1984 | Sabelman et al. |
| 4,470,317 | A | 9/1984 | Sabloewski et al. |
| 4,585,439 | A | 4/1986 | Michel |
| 4,883,472 | A | 11/1989 | Michel |

(Continued)

FOREIGN PATENT DOCUMENTS

DE  3609555  9/1987

(Continued)

*Primary Examiner*—Nicholas D Lucchesi
*Assistant Examiner*—Jason Flick
(74) *Attorney, Agent, or Firm*—Edward J. Prein (57) ABSTRACT

A medication dispensing apparatus having a gear set (62) to provide a mechanical advantage to the plunging of the apparatus plunger (64). The gear set has a first pinion (114) in meshed engagement with a rack (91) of the plunger, and a second pinion (126) in meshed engagement with a rack (80) of a drive member (68) of the apparatus. The gear set operatively interconnects the plunger and the drive member such that after the plunger is moved relative to the housing (30, 31) in proximal direction to prepare the apparatus for injection, the plunger, when distally moved, causes the drive member to advance in a distal direction to force medication through an outlet, typically provided with an injection needle (40), at the distal end (22) of the apparatus. An opening (130) through one of the pinions accommodates the drive member to allow for a compact apparatus.

17 Claims, 6 Drawing Sheets

U.S. PATENT DOCUMENTS

| | | | |
|---|---|---|---|
| 5,092,842 | A | 3/1992 | Bechtold et al. |
| 5,112,317 | A | 5/1992 | Michel |
| 5,300,041 | A | 4/1994 | Haber et al. |
| 5,304,152 | A | 4/1994 | Sams |
| 5,368,572 | A | 11/1994 | Shirota |
| 5,378,233 | A | 1/1995 | Haber et al. |
| 5,591,136 | A | 1/1997 | Gabriel |
| 5,722,956 | A | 3/1998 | Sims et al. |
| 5,728,074 | A | 3/1998 | Castellano et al. |
| 5,743,889 | A | 4/1998 | Sams |
| 5,782,633 | A * | 7/1998 | Muhlbauer .................. 433/90 |
| 5,807,334 | A | 9/1998 | Hodosh et al. |
| 5,814,022 | A | 9/1998 | Antanavich et al. |
| 5,913,843 | A | 6/1999 | Jentzen |
| 5,954,695 | A | 9/1999 | Sims et al. |
| 5,961,495 | A | 10/1999 | Walters et al. |
| 5,961,496 | A | 10/1999 | Nielsen et al. |
| 6,003,736 | A | 12/1999 | Ljunggren |
| 6,048,336 | A | 4/2000 | Gabriel |
| 6,074,372 | A | 6/2000 | Hansen |
| 6,096,010 | A | 8/2000 | Walters et al. |
| 6,110,149 | A | 8/2000 | Klitgaard et al. |
| 6,152,931 | A | 11/2000 | Nadal et al. |
| 6,159,161 | A | 12/2000 | Hodosh |
| 6,221,046 | B1 | 4/2001 | Burroughs et al. |
| 6,228,067 | B1 | 5/2001 | Gabriel |
| 6,245,046 | B1 | 6/2001 | Sibbitt |
| 6,280,421 | B1 | 8/2001 | Kirchhofer et al. |
| 6,537,251 | B2 | 3/2003 | Klitmose |
| 6,582,404 | B1 | 6/2003 | Klitgaard et al. |
| 6,585,699 | B2 | 7/2003 | Ljunggreen et al. |
| 6,599,272 | B1 | 7/2003 | Hjertman et al. |
| 6,620,137 | B2 | 9/2003 | Kirchhofer et al. |
| 6,663,602 | B2 | 12/2003 | Moller |
| 6,692,472 | B2 | 2/2004 | Hansen et al. |
| 6,716,198 | B2 | 4/2004 | Larsen |
| 2002/0049415 | A1 | 4/2002 | Fukuda |
| 2002/0107486 | A1 | 8/2002 | Munk |
| 2002/0188250 | A1 | 12/2002 | Landau et al. |
| 2003/0050609 | A1 | 3/2003 | Sams |
| 2004/0019326 | A1 | 1/2004 | Gilbert et al. |
| 2005/0222540 | A1 | 10/2005 | Kirchhofer et al. |

FOREIGN PATENT DOCUMENTS

| | | |
|---|---|---|
| GB | 27377 | 11/1914 |
| WO | WO 96/26754 | 9/1996 |
| WO | WO 00/51668 | 9/2000 |
| WO | WO 01/19434 | 3/2001 |
| WO | WO 01/95959 | 12/2001 |
| WO | WO 02/076535 A1 | 10/2002 |
| WO | WO 03/080160 A1 | 10/2003 |
| WO | WO 2004/004825 | 1/2004 |
| WO | WO 2004/020027 A1 | 3/2004 |
| WO | WO 2004/078239 A1 | 9/2004 |
| WO | WO 2004/078240 A2 | 9/2004 |

* cited by examiner

MEDICATION DISPENSING APPARATUS WITH GEAR SET HAVING DRIVE MEMBER ACCOMMODATING OPENING

This is the national phase application, under 35 USC 371, for PCT/US2005/010205, filed 25 Mar. 2005, which, claims the benefit, under 35 USC 119(e), of US provisional application 60/557,545, filed 30 Mar. 2004.

BACKGROUND OF THE INVENTION

The present invention pertains to medication dispensing devices, and, in particular, to a portable medication dispensing device such as an injector pen.

Patients suffering from a number of different diseases frequently must inject themselves with medication. To allow a person to conveniently and accurately self-administer medicine, a variety of devices broadly known as injector pens or injection pens have been developed. Generally, these pens are equipped with a cartridge including a piston and containing a multi-dose quantity of liquid medication. A drive member, extending from within a base of the injector pen and operably connected with typically more rearward mechanisms of the pen that control drive member motion, is movable forward to advance the piston in the cartridge in such a manner to dispense the contained medication from an outlet at the opposite cartridge end, typically through a needle that penetrates a stopper at that opposite end. In disposable pens, after a pen has been utilized to exhaust the supply of medication within the cartridge, the entire pen is discarded by a user, who then begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

One known type of injection pen uses a pull/push sequence applied to an externally accessible plunger member to deliver medication from the pen. The pulling of the plunger member in an axial, proximal direction first cocks or arms the pen for dose delivery, and then the axial pushing of the plunger member in the distal direction advances the cartridge piston to dispense the medication. While useful, such devices are not without their shortcomings. For example, some users who possess limited hand strength may find it difficult to apply sufficient force to push in the plunger member to inject a dose. In addition, the short plunger member travel associated with delivering very small doses in some pens may cause some users to question whether in fact a pen is operating to delivery the expected relatively small dose.

A number of injection pens are disclosed in International Publication No. WO 03/080160, the disclosure of which is incorporated herein by reference. These injection pens are advantageously designed with a mechanical advantage to allow lesser required plunger forces and greater plunger travel. However, when such pens offset the gear set from the axis of the cartridge, an asymmetrical injection pen may result if the overall pen size is minimized as is often desirable. Still further, the high mechanical advantages afforded by such pens may, under certain operating conditions, result in high forces being experienced by the internal gears or other components, which therefore may need to be made more robust to account for such forces.

Thus, it would be desirable to provide an apparatus that can overcome one or more of these and other shortcomings of the prior art.

BRIEF SUMMARY OF THE INVENTION

In one form thereof, the present invention provides a medication dispensing apparatus including a housing, a drive member within the housing and movable in a distal direction, a fluid container defining a medicine-filled reservoir with a movable piston at one end and an outlet at the other end, the piston being engageable by the drive member to be advanced toward the outlet when the drive member is moved distally, a plunger movable relative to the housing from a distal position to a proximal position, the plunger manually pushable relative to the housing in the distal direction to be shifted from the proximal position to the distal position, means for interconnecting the drive member and the plunger to convert motion of the plunger from the proximal position to the distal position into a lesser amount of motion of the drive member in the distal direction, the interconnecting means including a gear set including a first pinion in meshed engagement with a rack of the plunger and a second pinion in meshed engagement with a rack of the drive member, and wherein at least a portion of the drive member extends through an opening through at least one of the first and second pinions.

One advantage of the present invention is that a medication dispensing apparatus can be provided which is internally configured to utilize space efficiently to allow for a compact design that contributes to a small and symmetrical design of the apparatus.

Another advantage of the present invention is that a medication dispensing apparatus with a gear set can be provided in which a gear that does not fully revolve during use may be modified to eliminate extraneous gear teeth and accommodate passage therethrough of another component, such as within the plane of the provided gear teeth.

Still another advantage of the present invention is that a medication dispensing apparatus can be provided with a force absorbing limiter to limit the forces experienced by other components of the apparatus during use.

Still another advantage of the present invention is that a medication dispensing apparatus can be provided which mechanically prevents a user from causing an injection prior to properly cocking the pen to deliver a complete dose.

Yet another advantage of the present invention is that a medication dispensing apparatus can be provided which assists the user in consistently delivering a proper dose.

BRIEF DESCRIPTION OF THE DRAWINGS

The above-mentioned and other advantages and objects of this invention, and the manner of attaining them, will become more apparent, and the invention itself will be better understood by reference to the following description of embodiments of the invention taking in conjunction with the accompanying drawings, wherein.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Figure 1:
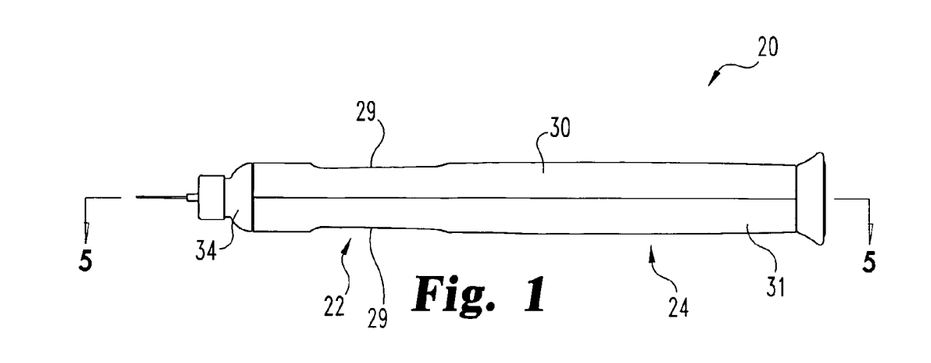
FIG. 1 is a front elevational view of a first embodiment of a medication dispensing apparatus of the present invention equipped with a pen-needle assembly, which apparatus is arranged in a ready or ready-to-be-cocked state.
Figure 2:
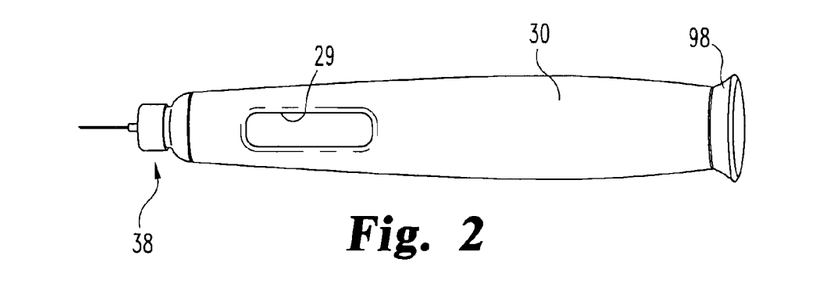
FIG. 2 is a top perspective view of the medication dispensing apparatus of FIG. 1.

Referring now to FIGS. 1 and 2, there is shown a first embodiment of a medication dispensing apparatus of the present invention. Any directional references in this detailed description with respect to FIG. 1 or any of the other Figures, such as right or left, up or down, or top or bottom, are intended for convenience of description, and by itself does not limit the present invention or any of its components to any particular positional or spatial orientation.

The apparatus, generally designated 20, is shown as an injector pen, which pen has an elongated, substantially writing instrument-like form, although other forms are within the scope of the invention. Medication injector pen 20 is a disposable pen, in that after the quantity of medicine contained therein is exhausted by multiple operations of the pen, the entire pen is discarded rather than being reset and reloaded with a replacement container of medicine. Pen 20 is repeatably operable to deliver into a user a fixed dose, i.e., a dose in a specific amount that is dictated by the particular design of the pen. For the shown pen 20, that fixed dose is not settable by a user but rather is dictated by the pen manufacturer.

Injector pen 20 generally includes a distal portion 22 and a proximal portion 24. Distal portion 22 contains the medicinal fluid to be outlet at its distal end upon pen operation. The outlet end of distal portion 22 is equipped in FIG. 1 with an injection needle, which needle is in an uncapped state. A needle-covering cap for the pen may be provided as is conventional. Proximal portion 24 contains the injecting mechanism used to force the contained medicine from the needled end.

Figure 4:
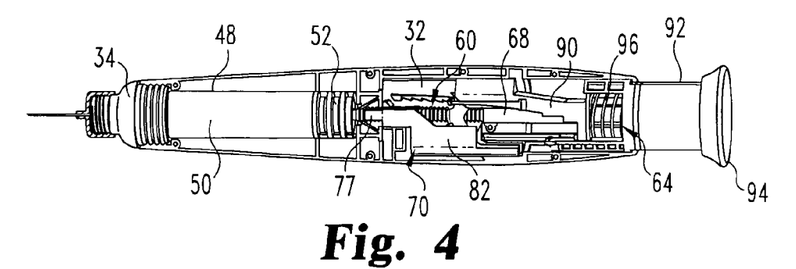
FIG. 4 is the medication dispensing apparatus of FIG. 3 with a piece removed to better show internal components of the apparatus.

The injecting mechanism housing is formed from a lightweight and opaque material, such as injection molded plastic, in two longitudinally extending halves 30 and 31. The housing halves 30 and 31 are aligned via mating pins and recesses provided therein and fixedly secured together during manufacture, such as via adhesives or ultrasonic welding. The injecting mechanism housing is somewhat elliptical in transverse cross-section to provide flatter regions in its circumference that aid in preventing pen 20 from rolling when placed upon a planer surface, and to accommodate the injecting mechanism in a limited volume form. The non-cylindrical tubular body of housing halves 30 and 31 defines an internal hollow 32 (See FIG. 4) in which the drive member extends in an axial or longitudinal direction.

Distal portion 22 includes a retainer that holds a cartridge 48 therein. The cartridge retainer is shown formed in part as a distal extension of the plastic housing for the injecting mechanism of the pen, and in additional part as a stepped-down plastic cap 34 that is fixed securely during manufacture, such as via adhesives or ultrasonic welding, into the housing extension distal end. Although cap 34 is shown, for example, in FIG. 4 as being threaded to the housing extension distal end, such threading is not required. Openings or windows 29 in the distal extension of each of housing halves 30 and 31 allow the usable contents of the cartridge to be seen. The open, stepped-down distal end of cap 34 is provided with external threading, or other suitable connection means, to releasably connect a pen-needle assembly, generally designated 38.

Figure 5:
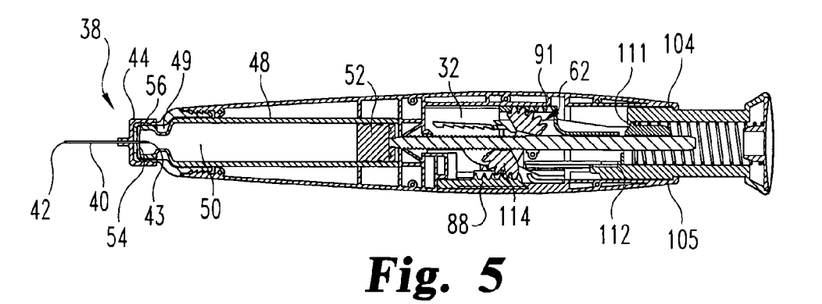
FIG. 5 is a longitudinal cross-sectional view of the medication dispensing apparatus of FIG. 3, which view is conceptually taken along line 5-5 of FIG. 1.

With reference to FIG. 5, pen-needle assembly 38 is of known design and includes a double-ended needle cannula or injection needle 40 having a distal tip 42 at one end and a proximal point 43 at the other. Injection needle 40 is mounted in a tubular hub 44 that is internally threaded to cooperate with the retainer cap design so as to be screwable onto and off of the threading of the retainer cap. Other types of connection types, including a snap on connection, may be provided between the needle assembly and the cap. Tip 42 may be protected by a not shown tubular cap mounted to the hub, as well as a not shown pen cap releasably attachable to, for example, the retainer, which cap(s) is removed when pen 20 is used to inject medicine. Although the needle assembly is shown as having a single injection needle, needle assemblies which may be used with pen 20 may be of various types known in the art, including, but not limited to, assemblies with one or more shortened injection needles, including microneedle arrays.

Cartridge 48 is of conventional design and defines a medicine-filled reservoir 50 that is closed at its proximal end by a piston 52 that is axially slidably and sealably engaged with the cartridge interior wall to hold the fluid medication within reservoir 50. The distal, outlet end of cartridge reservoir 50 is sealed by a septum 54 held by a cap 56 that is secured to a stepped-down diameter neck portion 49 of the cartridge. When pen-needle assembly 38 is mounted on retainer cap 34, the proximal point 43 of injection needle 40 penetrates cartridge septum 54 to provide a fluid flow outlet by which medicine within cartridge reservoir 50 can be dispensed from needle tip 42 during operations of injector pen 20. Cartridge 48 is sandwiched between the interior surface of cap 34 and an internal shoulder provided on housing halves 30 and 31 to prevent axial movement of the cartridge during use. Other manners of capturing the cartridge relative to the housing may alternatively be employed.

The fluid medicine container shown and described above is illustrative and not intended to be limiting as other constructions may be employed within the scope of the invention. For example, rather than the shown container in which a distinct cartridge is held via a cap within a retainer region of the pen housing, in another fluid container embodiment, the cartridge could be constructed to be sufficiently durable and adapted to secure directly to a pen proximal portion 24 without any protective retainer region therearound, and with the pen-needle assembly directly mountable to the cartridge. Still further, the cartridge could be held in a retainer distinct from the pen housing, which cartridge/retainer assembly is, in the case of a disposable pen, fixedly mounted or secured, via adhesives, ultrasonic welding or in another suitable manner, to a previously subassembled pen proximal portion 24 when injector pen 20 is assembled by the manufacturer, or, in the case of a reusable pen, removably mounted or secured, such as via a threaded connection, to a reusable pen proximal portion 24 having a resettable drive member.

With additional reference to FIGS. 3-7, pen proximal portion 24 of injector pen 20 includes an axially advanceable drive member generally designated 60, a gear set generally designated 62, and a plunger member generally designated 64.

Drive member 60 is formed in the shown embodiment of a multi-part construction including a foot 66, a cartridge-engaging piece 68 and a pinion-engaging piece 70. Foot 66 is disc-shaped and during manufacturing assembly is snap-fit to the distal end of drive member piece 68. Drive member piece 68 extends axially, has a square rod-shaped body, and during medicine injecting causes movement of the cartridge piston that it engages via the foot, which piston movement is the same in distance and direction as its movement. Foot 66 has a larger surface area than the transverse cross-sectional area of drive member piece 68 to distribute loading on the cartridge piston 52 that foot 66 contacts and thereby directly engages during piston advancing.

Drive member pieces 68 and 70 are constrained by the internal shaping of housing halves 30 and 31 to be axially translatable and rotatably fixed therein. Cartridge-engaging piece 68 is movable in the distal direction and prevented from proximal movement relative to the housing halves, while pinion-engaging piece 70 is clutchably connected to cartridge-engaging piece 68 to be moveable relative thereto in a proximal direction but not the distal direction. To provide for these one-way axial motions, ratchets are employed in the shown embodiment, but other elements may be used. For example, a hard but compliant toothed member or members, such as made of metal, may be provided in tight engagement with a smooth, such as cylindrical, and relatively soft member lacking surface features, which metal tooth/teeth are arranged such that motion of the other member in only a single direction is permitted, as in the opposite direction the tooth/teeth dig into and deform the relatively soft surface to create a wedging action that impedes further motion in that direction.

In the shown embodiment, cartridge-engaging piece 68 includes a row of ratchet teeth on each of its four sides, which teeth continue uninterrupted along a portion of its axial length. The axial positioning and length that each row of teeth must span along its respective side is a function of the various pawls' positioning and intended use, such as the total injection volume and number of discrete injections, of pen 20. Rows of ratchet teeth 73a on opposite sides of drive member piece 68 have a one-way ramping and are engaged by a pair of diametrically opposed resilient tabs or pawls 75 extending inward from the housing near the distal end of proximal portion 24. The resilient pawls 75 slide along and over teeth 73a when drive member piece 68 is advanced distally during use, but abut the transverse, proximal face of teeth 73a to prevent drive member back-up in the proximal direction.

Rows of ratchet teeth 73b on the other two sides of drive member piece 68 are also provided with a one-way ramping similar in direction to the ramping of teeth 73a, and are engaged by a pair of diametrically opposed resilient pawls 77 on pinion-engaging piece 70. As described further below, pawls 77 slide along and over teeth 73b when pinion-engaging piece 70 is moved proximally during pen cocking, but abut teeth 73b during the distal advancement of pinion-engaging piece 70 during injection, which abutting results in pinion-engaging piece 70 shifting distally cartridge-engaging piece 68. The pitch or distance between the transverse face of each adjacent tooth 73b preferably is the distance piston 52 needs to be advanced to deliver the pen's fixed dose. And, while teeth 73a are shown as being equal in length to teeth 73b, teeth 73a could be an integer multiple shorter.

Drive member piece 68 is shown as being integrally provided with its ratchet teeth 73a and 73b, such as by being made of a one-piece plastic injection molding, or a one-piece metal part. Other constructions of drive member piece 68, such as an assembly of separately formed component parts, are within the scope of the invention.

Although two pawls 75 and two pawls 77 are shown, each integrally formed with the housing or the drive member piece 70 as applicable, different numbers of pawls, including as few as a single pawl for anti-backup and a single pawl for advancement which cooperate with one or more rows of ratchet teeth, may be provided, and further the pawls may be separately formed and then tied to the housing or drive member piece 70 as applicable to be longitudinally fixed relative thereto.

Pinion-engaging piece 70 includes a pair of laterally spaced, longitudinally extending racks 80. Racks 80 are provided along an interior surface of the body 82 of drive member piece 70. Pawls 77 resiliently extend from body 82, and pawls 77, body 82 and racks 80 are integrally formed from an injection molded plastic, although other constructions may also be suitable.

To minimize the diameter of pen 20, this rack member and other rack members can be of such a small size that the base of the teeth of the rack is provided with openings through the rack member to accommodate the radial outer extent of the teeth of a pinion with which it meshes.

Figure 6:
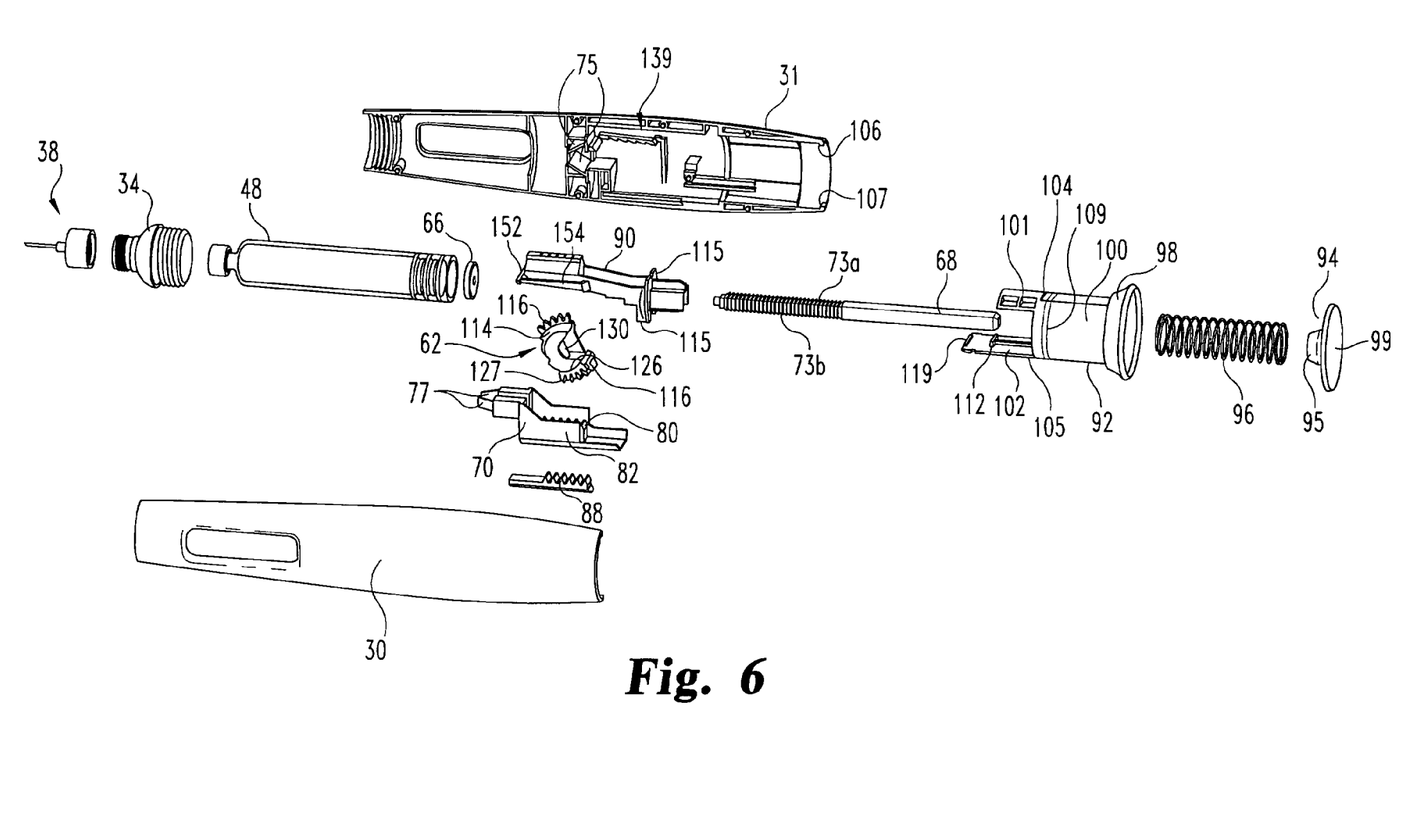
FIG. 6 is a perspective, exploded view of the medication dispensing apparatus of FIG. 1.
Figure 7:
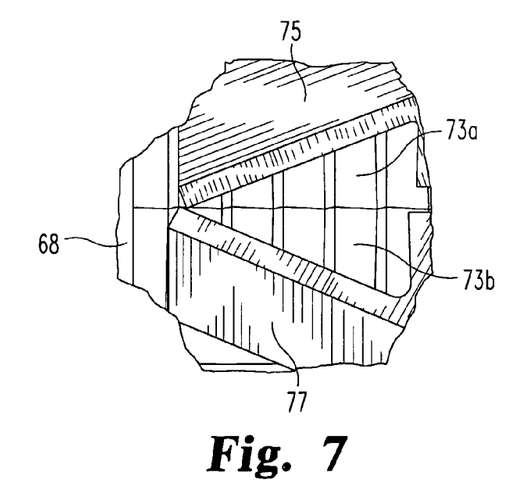
FIG. 7 is a partial view of select portions of the apparatus of FIG. 2.

As further shown in FIGS. 5 and 6, a fixed or axially stationary rack 88 is included within pen proximal portion 24. In the shown embodiment, rack 88 is provided in the form of an insert that, during manufacturing assembly, is installed within a corresponding channel defined by housing halves 30 and 31, and which rack is axially fixed therein, such as by adhesives or other suitable manner including an interference fit. While one such rack 88 is shown and works in conjunction with the single larger diameter pinion 114 of gear set 62 described below, additional fixed rack elements could also be provided, or could be offset laterally from the position shown in FIG. 5. Still further, the axially fixed rack could be integrally formed with one or more of the housing halves, although such may complicate manufacture or assembly.

Plunger member 64 allows a user to control the internal gear set of the apparatus to prepare pen 20 for injection, as well as to effect the injection. In the shown embodiment, plunger member 64 is formed of a multi-piece construction, including an input element 90, a button 92, a button cap 94 and a force limiting biasing member 96.

Button 92 is molded from plastic and has an open proximal end in which a plastic button cap 94 can be snapped, glued, ultrasonically welded or otherwise fixedly attached in a conventional manner. A grip portion 98 of button 92 extends proximally of housing halves 30 and 31, even when apparatus 20 is arranged in a ready-to-be-cocked position. Grip portion 98 is externally accessible to be manually pulled by a user for pen cocking purposes. Grip portion 98 is shown as having an outwardly flared knob shape so as to be more readily grasped by a user, such as between the thumb and fingers of a user, when pulled to the right from the perspective of a viewer of FIG. 1. Other graspable grip portion configurations may be substituted, such as a loop in which a finger can insert, or a bar under which fingers can be looped. The proximal end 99 of cap 94 serves as a push surface against which a force can be manually applied to push the plunger member of a cocked pen to the left from the perspective of a viewer of FIG. 3.

Figure 3:
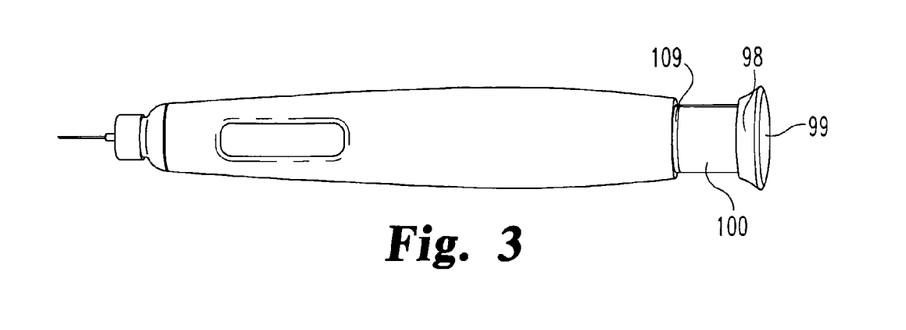
FIG. 3 is the medication dispensing apparatus of FIG. 2 after being manipulated from its ready state to a cocked or ready-to-inject state.

A tubular portion 100 of plunger button 92 extends distally from grip portion 98 and telescopically fits within housing interior hollow 32 so as to be slidable into and out from such hollow during use of pen 20. Tubular portion 100 is generally elliptical in transverse cross-section and conforms closely to the housing shape at its distal end such that button 92 is rotatably fixed with the housing. Flanges 101 and 102 extend from the proximal end of tubular portion 100. The outward faces of flanges 101 and 102 include curved ribs 104 and 105 that, during pen cocking, abut inward lips 106 and 107 formed into the distal ends of housing halves 30, 31 to limit withdrawal of the plunger member from the housing. An indicating band 109 that rings tubular portion 100 visibly projects beyond the proximal end of the pen housing when plunger button 92 has been fully withdrawn to properly cock pen 20, as shown in FIG. 3. Indicating band 109 is preferably a ring of color that contrasts with the different colors of the housing and button so as to be readily visible by a user during use to indicate that the complete cocking of the pen has occurred. The inward faces of flanges 101, 102 include latches 111, 112 that snap-fit during manufacturing assembly over transversely extending shoulders 115 of an injection molded plastic input element 90 to prevent axial, proximal withdrawal of the button 92 from the input element during operation. An inward lip 119 at the distal end of flange 102 may be used in locking the pen after its final dose has been administered, as described further below.

The inward face of plastic plunger element 90 includes a rack 91 that, similar to fixed rack 88, works in conjunction with larger diameter pinion 114 of gear set 62. The shape of plunger element 90 and the hollow interior of tubular portion 100 accommodate the proximal end of drive member piece 68. The outer periphery of plunger element 90 is non-circular and fits closely within the correspondingly shaped housing halves to aid in preventing plunger rack rotation during use.

Axially extending within the central bore of plunger button 92 is a force limiting biasing member 96 provided in the form of a metal, helically coiled compression spring. Other suitable biasing elements may alternatively be employed. During pen manufacture, spring 96 is captured within button 92 with one spring end in abutting contact with the proximal face of shoulder 115, and the other spring end in abutting contact with the distal face of button cap 94 around centering hub 95. Spring 96 is so captured in a pre-stressed, or partially compressed, state. The extent of the pre-stressing is at least as large as forces the manufacturer expects users to apply on the plunger button during normal plunging to achieve proper pen operation. In one embodiment, the pre-stressing is in an amount of 1.2 pounds. Thus, during normal plunging, the spring does not further compress and the button 92 and input element 90 shift as a unit and without relative axial motion.

Figure 12:
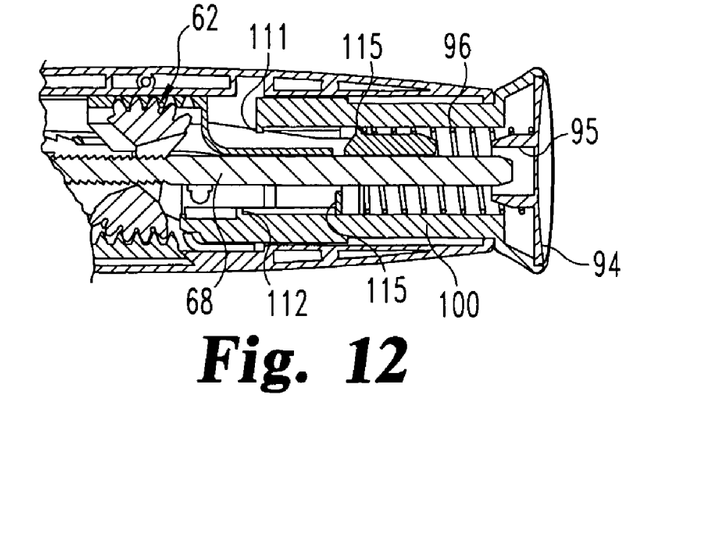
FIG. 12 is a partial cross-sectional view showing an internal configuration of the pen components when a partially cocked medication dispensing apparatus is being plunged.

Coil spring 96 is also designed with sufficient spacing in its coiling, and with proper elastic properties, such that the spring, by compression, can accommodate movement of button 92 from the cocked position, shown in FIG. 3, to the ready-to-be-cocked position, shown in FIG. 1, without movement of plunger element 90. As a result, spring 96 can absorb until the force is released, rather than transfer to internal components of the device, any forces which, possibly due to the mechanical advantage afforded by pen 20, could damage the internal components. For example, if forces in excess of 14.4 pounds were to be avoided on the drive member if the button 92 were manually plunged after pen 20 had been only partially cocked, for a pen providing a 12 to 1 mechanical advantage, spring 96 would be designed to compress toward the arrangement shown in FIG. 12 upon greater than 1.2 pounds of force manually applied to cap 94. In this situation, as soon as the user removes the plunging force that has depressed the plunger button 92, the spring will cause the plunger button to return to its extended position, and this return indicates to the user that an injection has not been completed. Such a plunger button motion also may occur if a user attempts to plunge with a fully cocked pen, but has forgotten to mount a pen-needle assembly 38 to the pen distal end, or such needle is blocked. In another situation where a needle equipped pen has been completely cocked and the pen plunger button has been plunged with too large of a force so as to compress the spring 96, and the user continues to hold the plunger button in its depressed state, the spring 96 can extend, thereby forcing the plunger element 90 distally to force medication from the pen in a normal fashion, with the pen spring continuing to extend until returning to its normal pre-stressed state, at which point the pen will have completed administrating the dose in a suitable fashion and will be arranged as shown in FIG. 1. In alternate embodiments in which the remainder of the pen is designed to be sufficiently robust for forces reasonably expected to be applied to the plunger, the force limiting spring can be eliminated, and the button 92 and plunger element 90 can be integrally formed, or assembled from multiple parts in a non-axially shifting relationship.

The gear set utilized in the injection pen is configured to convert plunger member motion of a first distance into drive member motion of a second distance less than the first distance. The gear set shown at 62 is made from a lightweight material such as plastic, and utilizes first and second sized pinions that can travel linearly as well as rotate, which linear motion can occur relative to all of the plunger, the drive member and the housing.

The larger pinion 114 is centered within the pen height and is flanked by a pair of smaller pinions 126 in the shown embodiment, but such an arrangement and number of pinions merely provides a well-balanced gear set and is not necessary to practice the invention.

The first or larger sized pinion 114 includes a discontinuous or interrupted ring of external teeth. Circumferential gaps between the toothed sections are formed by an opening 130 extending completely through the pinion diameter within the plane of the gear teeth, which plane is perpendicular to the axis of rolling rotation of the pinion. Opening 130 divides the first pinion into two arcuate sections of external gear teeth 116, one of which meshes with housing rack 88 and the other section meshes with plunger rack 91. Since the two arcuate sections of teeth 116 do not revolve into contact with each other's rack, these arcuate toothed sections need not have identical pitch and/or width, provided such sections have the same pitch diameter. Moreover, the non-circular shape of pinion 114 that results from opening 130 allows the overall axial length of the device to be reduced. Cartridge-engaging piece 68 can pass freely through opening 130 and does not interfere with the operation of the gear set as opening 130 replaces external teeth that are not needed due to the small angle of revolution of the pinion necessary for pen use, which small angle or partial roll is possible due to the high mechanical advantage possible with the gear design. The passage of the drive member through the center of the pinion allows apparatus 20 to be symmetrical about the cartridge axis and to have a compact design.

Pinions 126 have the same axis of rolling rotation as pinion 114 and each includes external gear teeth 127 arranged with a pitch diameter that is less than the pitch diameter of gear teeth 116. Gear teeth 127 meshably engage drive member racks 80, which racks 80 are parallel to plunger rack 91 but disposed on the opposite side of the pinion axis. As with the gear teeth 116 of pinion 114, gear teeth 127 are discontinuous as during use pinion 126 experiences but a partial revolution and therefore only a short arc of teeth to mesh with the rack are required.

Although pinion 114 and pinions 126 are shown integrally formed, these components can be separately formed and assembled together so as to be corotatable. In the shown embodiment, the pinions are formed as essentially being an open box in shape, but the pinions can be differently formed, such as C-shaped. Opening 130 does not pass through the plane of pinions 126 in the shown embodiment, but in alternate embodiments in which the relative positions of the pinions are switched, with corresponding switching of the racks, the opening could pass through the smaller diameter pinion.

In order to limit user misuse, pen 20 preferably includes a partial-cocking-preventing guide and follower. In embodiments where partial dosing is of lesser concern, such guide and follower need not be provided. The partial-cocking-preventing mechanism prevents an injection until the plunger has been manually shifted to the proximal or completely withdrawn position that corresponds to a fully cocked position of pen 20.

Figure 8:
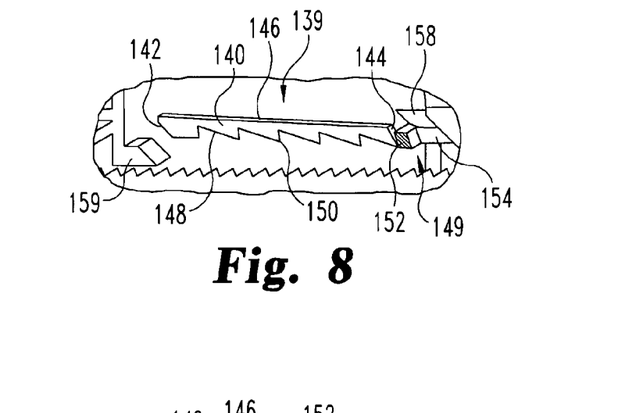
FIG. 8 is a partial view of select portions of the apparatus of FIG. 4 showing the partial-cocking-preventing racetrack and follower of the present invention, wherein such portions are still shown arranged in a cocked state.

One suitable form of guide and follower is better shown in FIG. 8 and includes a guide or racetrack, generally designated 139, and a follower, generally designated 149. Guide 139 includes a bar portion 140 that is integrally formed with housing half 31 and which inwardly projects therefrom into hollow 32. A mirror image bar portion may similarly be provided on housing half 30. Rather than being integrally formed, the bar portion 140 may be separately formed and fixedly assembled to the housing during manufacture.

Bar portion 140 includes an angled, distal end 142 and an angled, proximal end 144. The top face of bar portion 140 shown in FIG. 8 provides a flat travel surface 146, and the opposite or bottom face of bar portion 140 includes a travel surface 148. At least one, and preferably a plurality of, ratchet teeth 150 are provided on the travel surface 148 and interrupt the otherwise flat surface.

The follower 149 is associated with the plunger member and includes a pawl that cooperates with the ratchet teeth 150 to prevent distal movement of the plunger when the follower pawl is in engagement with the travel surface 148 via an abutting relationship with any one of teeth 150. In the shown embodiment, the follower pawl is in the form of a transversely extending pawl 152 that spans and is supported by resilient arms 154 that flank and distally project from the body of input element 90. Arms 154 and pawl 152 are integrally molded with the plastic input element 90, but may be otherwise formed.

Figure 10:
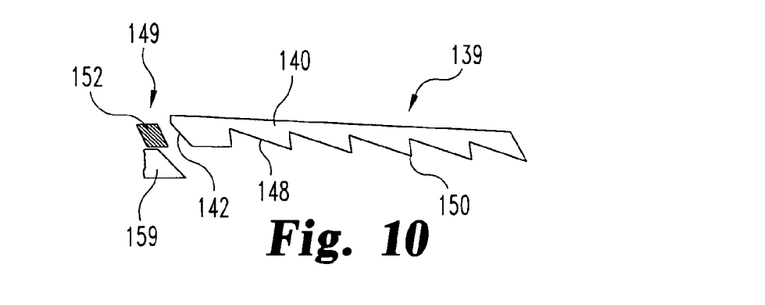
FIG. 10 is a two-dimensional representation conceptually similar to FIG. 9, but wherein the portions are shown arranged at a final stage of dose injection.
Figure 11:
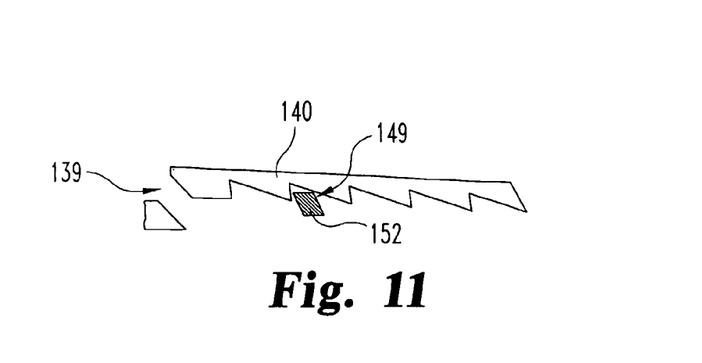
FIG. 11 is a two-dimensional representation conceptually similar to FIG. 9, but wherein the portions are shown arranged at an intermediate stage of pen cocking.

Referring now to FIG. 10, there is abstractly shown the guide 139 and the follower 149 oriented in an arrangement associated with the ready-to-be-cocked position of pen 20. Follower pawl 152 is positioned such that when plunger member 64 is manually pulled proximally, pawl 152 is first cammed downward by distal end 142, and then slides along travel surface 148 by sliding up along and snapping over the ratchet teeth 150. As pawl 152 snap passes over each of the teeth 150, the interaction of the pawl with that passed ratchet tooth then prevents distal travel of the plunger element 90 therefrom prior to complete pen cocking. At an intermediate point of pen cocking, follower 149 and guide 139 are arranged as shown in FIG. 11. As plunger withdrawal continues, pawl 152 reaches the end of travel surface 148 and, due to the built-in resiliency of its arms 154, snaps upward until part of the follower abuts another guide element in the pen. For example, an angled shoulder 158 molded into the housing is abutted by the pawl 152. This snap action of the pawl 152 against shoulder 158 provides an audible click that can indicate to the user that plunger withdrawal has been completed, and the timing of the click would correspond to indicating band 109 of button 92 becoming visibly exposed to the user. At this point, follower 149 and guide 139 are arranged as shown in FIG. 8.

Figure 9:
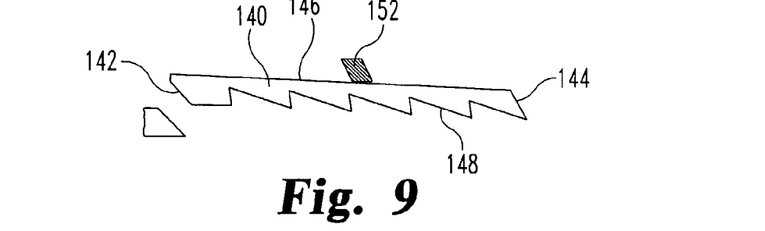
FIG. 9 is a two-dimensional representation of the racetrack and follower shown in FIG. 8, wherein such portions are shown arranged during the process of plunger advancement to cause injection.

When the plunger member is subsequently manually depressed for injection, the distal face of pawl 152 encounters and must be cammed upward by its engagement with proximal end 144 of guide bar 140, and the angled shape of shoulder 158 allows this movement. This camming upward provides an overcomeable resistance that may serve to limit unintended ejections of medicine. After the pawl is so cammed upward, it continues to slide along, and in the shown embodiment slides directly in contact with, travel surface 146. At this point, follower 149 and guide 139 are arranged as shown in FIG. 9. It will be appreciated that ratchet teeth facing in the direction opposite to ratchet teeth 150 can be provided on travel surface 146 if it is desired to prevent the input rack from being withdrawn in the middle of an injection and prior to the completion of the injection, or to provide clicks during injection. Follower pawl 152 continues to slide along travel surface 146 until the plunger has been distally advanced sufficiently such that pawl 152 snaps down over the distal end 142 of bar portion 140 and into abutting contact with guide shoulder 159, which may be integrally formed with the housing. This abutting contact provides an audible click indicating to a user that the injection is complete. This end of injection clicking noise corresponds to the time at which portions of the pen abut to halt further plunger advancement. Such pen portions are appropriately chosen, such as based on tolerance stack up, and may be the distal face of grip portion 98 abutting the proximal face of housing pieces 30, 31. At this point, the guide and follower have returned to the arrangement shown in FIG. 10.

In some situations, it may be desirable to provide injection apparatus 20 with a feature that prevents use of the apparatus after a particular number of doses have been administered thereby, or when the medicine supply is exhausted. For example, for a therapeutic having a stated life of four weeks after the first puncturing of its cartridge septum by a pen-needle assembly, it may be desirable for a once-a-day injector pen loaded with that therapeutic to be disabled after the twenty-eighth injection is complete. To that end, any of a variety of mechanisms may be provided to prevent the plunger from being withdrawn, either at all or completely, after the twenty-eighth and "final" dose has been administered. Alternatively, and preferably if an alert were also included to notify the user thereof, the mechanism may cause cocking/plunging movement of the plunger to have no effect after the "final" dose is administered.

Figure 13:
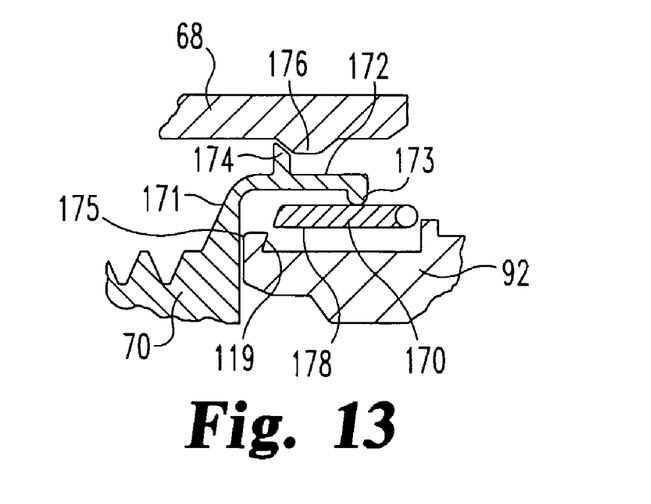
FIGS. 13, 14, 15 and 16 abstractly show elements which may be provided to lock the apparatus after the final intended dose has been administered to prevent a continued use of the apparatus.

For example, in the embodiment abstractly shown in FIG. 13, a mechanical lock is provided which activates during the injection of the final dose, which locking prevents the plunger from being withdrawn thereafter. FIG. 13 illustrates portions of the apparatus immediately prior to it being cocked to administer the final dose. A lock bar 170 is mounted on the injecting mechanism housing to be pivotable between a neutral, detented position shown, and a locking position. The drive member pinion-engaging piece 70 includes a support 171 from which proximally extends a resilient cam arm 172. Cam arm 172 includes a housing cam 173 at a proximal end, and a cammable protuberance 174 nearer its distal end, which protuberance is engageable with a cam 176 projecting from drive member cartridge-engaging piece 68. When plunger button 92 is moved proximally to cock pen 20 for the final dose, which movement shifts drive member piece 70 a lesser amount proximally while drive member piece 68 remains motionless, cam 176 contacts cammable protuberance 174 to force cam arm 172 downward, which in turn cams or pivots lock bar 170 downward. The button 92 is then moved distally to administer the final dose, which movement shifts drive member pieces 68 and 70 distally a lesser amount, and during which button movement the distal face 175 of lip 119 slides along and cams upward the underside 178 of lock bar 170, thereby camming up cam 173 and resilient arm 172 sufficiently to allow button 92 to pass distally until the lock bar, due to the returning tendency of arm 172, snaps into a latching relationship with a proximal face of lip 119. Subsequent attempts to pull out plunger 64 to cock the pen are thereby thwarted as the plunger is locked to the housing.

Figure 14:
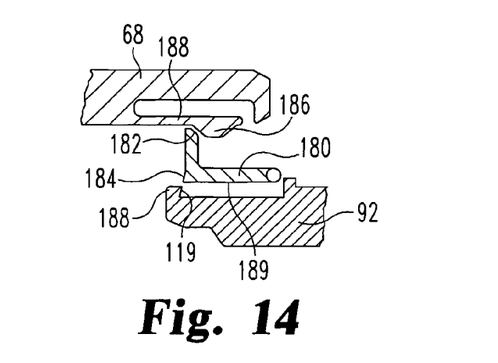

FIG. 14 abstractly shows another embodiment of a mechanical lock that activates during the injection of the final dose, which lock is shown immediately prior to the pen being cocked to administer the final dose. An L-shaped lock bar 180 is mounted on the injecting mechanism housing to be pivotable between a neutral, detented position shown, and a locking position. Lock bar 180 includes a cammable surface 182 with a truncated distal region, and a latching surface 184. A cam 186 is provided on a resilient arm 188 integrally molded with drive member cartridge-engaging piece 68. When plunger button 92 is moved proximally to cock pen 20 for the final dose, which movement shifts drive member piece 70 a lesser amount proximally while drive member piece 68 remains motionless, cam 186 contacts cammable surface 182 to pivot lock bar 180 downward. When plunger button 92 of the cocked pen is then moved distally to shift drive member pieces 68 and 70 distally to administer the final dose, the distal face 188 of lip 119 slides along and cams upward the underside 189 of lock bar 180, thereby camming up cam 186 and resilient arm 188 sufficiently to allow button 92 to pass distally until latching surface 184, due to the returning tendency of arm 188, snaps into a latching relationship with a proximal face of lip 119 to thereby lock the plunger to the housing.

Figure 15:
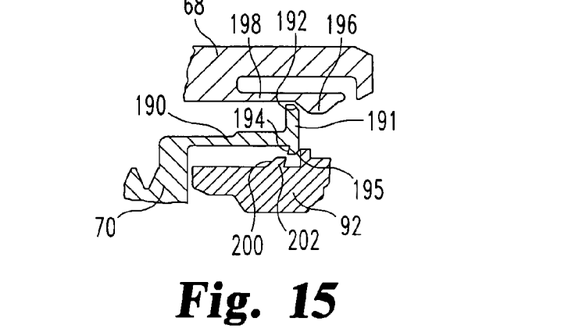

FIG. 15 abstractly shows another embodiment of a mechanical lock that activates during the injection of the final dose, which lock is also shown immediately prior to the pen being cocked to administer the final dose. The drive member pinion-engaging piece 70 includes a flexible arm 190 with a proximal, transversely oriented flange 191 having a cammable surface 192 at an upper end of the flange and a latching surface 194 and a button cammable surface 195 at the flange lower end. A cam 196 is provided on a resilient arm 198 integrally molded with drive member cartridge-engaging piece 68. When plunger button 92 is moved proximally to cock pen 20 for the final dose, which movement shifts drive member piece 70 a lesser amount proximally while drive member piece 68 remains motionless, cam 196 contacts cammable surface 192 to force arm 190 and thereby flange 191 downward. When plunger button 92 of the cocked pen is moved distally to shift drive member pieces 68 and 70 distally to administer the final dose, the sloped, distal face 200 of latch 202 engages flange surface 195 to cam upward flange 191 and thereby cam 196 and resilient arm 198 sufficiently to allow button 92 to pass distally until the flange latching surface 194, due to the returning tendency of arms 190 and 198, snaps into a latching relationship with latch 202. Subsequent attempts to pull out plunger 64 to cock the pen are thereby mechanically prevented as button 92 and drive member piece 70 are locked together.

Figure 16:
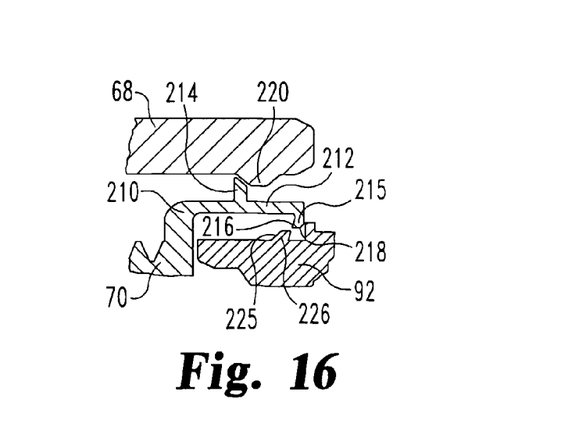

FIG. 16 abstractly shows yet another embodiment of a mechanical lock that activates during the injection of the final dose, which lock is also shown immediately prior to the pen being cocked to administer the final dose. The drive member pinion-engaging piece 70 includes a support 210 from which distally extends a resilient cam arm 212. Cam arm 212 includes a cammable protuberance 214 nearer its distal end, and at its proximal end an inward projection 215 including a latching surface 216 and a button cammable surface 218. Cam 220 is provided on drive member cartridge-engaging piece 68. When plunger button 92 is moved proximally to cock pen 20 for the final dose, which movement shifts drive member piece 70 a lesser amount proximally while drive member piece 68 remains motionless, cam 220 contacts cammable protuberance 214 to force arm 212 and thereby projection 215 downward. When plunger button 92 of the cocked pen is moved distally to shift drive member pieces 68 and 70 distally to administer the final dose, the sloped distal face 225 of latch 226 engages surface 218 to cam upward projection 215 and resilient arm 212 sufficiently to allow button 92 to pass distally until the projection latching surface 216, due to the returning tendency of arm 212, snaps into a latching relationship with latch 226 to thereby lock together button 92 and drive member piece 70.

In still other embodiments, different types of locking mechanisms may be employed to prevent use after the final injection. For example, the plunger element 90 may be physically locked, such as via a locking element, when cartridge-engaging piece 68 is driven distally to complete its final injection. For example, this plunger element locking feature may involve a spring-loaded locking element, mounted to the housing, that has a finger that slides along the proximal or untoothed portion of the body of drive member piece 68 during normal uses, which finger slides or falls off the proximal end of drive member piece 68 only during the administration of the final injection. This falling off of the finger allows the spring induced pivoting of the locking element to cause a portion of the pivoting locking element, or to cause the actuation of an additional locking element, to lockingly engage with a complementarily designed feature of plunger element 90.

The structure of injector pen 20 will be further understood in view of the following explanation of its operation. Initially, a user requiring a dose of medication will locate pen 20, which pen is typically in the ready arrangement shown in FIG. 1, which is the arrangement in which the pen remained after its previous use, or in which the pen is provided to a user for its first use.

A pulling step is first performed to cock or prepare the uncocked pen 20 to deliver the dose for which it has been designed. During that pulling or withdrawing step, and while the pen housing and/or distal portion 22 is grasped in one hand, a user uses her other hand to pull plunger grip portion 98 axially away from the pen housing. Plunger grip portion 98 is to be pulled proximally a fixed distance, specifically until the proximal faces of plunger ribs 104, 105 abut the distal faces of housing lips 106, 107, which abutment halts the axial movement of plunger member 64 and at which time band 109 is visible.

During this plunger withdrawal, gear set 62 operates in the following manner. Pinion 114 is caused to roll proximally in meshed engagement with fixed rack 88 and rack 91, and consequently pinion 126 moves proximally an equal distance. This proximal movement of pinion 126 involves pinion 126 rolling in meshed engagement with drive member rack 80, during which time pinion 126 simultaneously pulls pinion-engaging piece 70 proximally relative to piece 68 held by pawls 75, as pawls 77 each slide along and ultimately snap over a ratchet tooth 73b. The plunger member travel is designed such that the travel of the pinion engaging piece during a proper or complete pen cocking is just slightly greater than the spacing between successive teeth 73b, such that the pawl is assured of passing over a single tooth.

To actually inject the medicine, after pen 20 is manipulated so the injection needle distal tip 42 properly penetrates, for example, a user's skin, an axial, distal plunging force is applied to force plunger 64 distally. As plunger 64 starts to move distally, the travel of rack 91 causes larger pinion 114 to begin to roll along fixed rack 88. Pinions 126 simultaneously begin to roll along drive member rack 80. Due to the differences in pinion diameters, drive member rack 80 and therefore drive member piece 68, due to the abutting engagement of pawls 77 with teeth 73b, are forced to move in a distal direction, and drive member piece 68 motion advances piston 52 in the distal direction to force medication in reservoir 50 through injection needle 40 into the user. The injection is completed when the plunger 64 advancement is physically halted by abutting pen parts, immediately prior to which time the end of dose audible click has been made by pawl 152, at which time pen 20 is once again arranged in the ready or ready-to-be-cocked state shown in FIGS. 1 and 2.

Pen 20 can continue to be used to deliver its fixed dose until, for example, a locking feature prevents plunger withdrawal. At such time, pen 20 is to be disposed of and replaced with a similar but entirely new pen.

While this invention has been shown and described as having preferred designs, the present invention may be modified within the spirit and scope of this disclosure. This application is therefore intended to cover any variations, uses or adaptations of the invention using its general principles. For example, the force limiting feature provided by the multi-part plunger including the captured spring advantageously may be employed in other injection pens that include different and known mechanisms to provide a mechanical advantage between the plunger and the drive member. Still further, in an embodiment in which an injection spring is provided to cause drive member advancement in the injection process, the plunger could be provided with a trigger mechanism that, when the pen has been cocked and a small force is applied to the trigger mechanism, triggers the injection spring to further advance the plunger to operate the remainder of the pen to inject the medication. In such an embodiment, the trigger mechanism or plunger may include a display which disappears as the spring advances the plunger to notify a user when the injection has been completed by the injection spring. Further, this application is intended to cover such departures from the present disclosure as come within known or customary practice in the art to which this invention pertains.

We claim:

1. A medication dispensing apparatus comprising:
   a housing;
   a drive member within said housing and movable in a distal direction;
   a fluid container defining a medicine-filled reservoir with a movable piston at one end and an outlet at the other end, said piston engageable by said drive member to be advanced toward said outlet when said drive member is moved distally;
   a plunger movable relative to said housing from a distal position to a proximal position, said plunger manually pushable relative to said housing in the distal direction to be shifted from said proximal position to said distal position;
   means for interconnecting said drive member and said plunger to convert motion of said plunger from said proximal position to said distal position into a lesser amount of motion of said drive member in said distal direction, said interconnecting means including a gear set including a first pinion in meshed engagement with a rack of said plunger and a second pinion in meshed engagement with a rack of said drive member; and
   characterized in that at least a portion of said drive member extends through an opening through at least one of said first and second pinions, said opening extending completely through a diameter of said at least one of said first and second pinions.

2. The medication dispensing apparatus of claim 1 wherein said first pinion comprises said opening, wherein plunger rack engaging teeth of said first pinion are coplanar with said at least a portion of said drive member extending through said opening, whereby said rack engaging teeth do not extend continuously around said first pinion.

3. The medication dispensing apparatus of claim 2 wherein an axis of rolling rotation of said first pinion extends through said opening and is oriented generally perpendicular to said at least a portion of said drive member extending through said opening.

4. The medication dispensing apparatus of claim 2 wherein said plunger rack engaging teeth are arranged with a larger pitch diameter than a pitch diameter of drive member rack engaging teeth of said second pinion.

5. The medication dispensing apparatus of claim 2 wherein said drive member includes a first part and a second part, said drive member first part movable in a distal direction, said drive member second part clutchably connected to said first part to be moveable relative thereto in a proximal direction but not the distal direction, said second part comprising said rack in meshed engagement with said second pinion, wherein said first part comprises at least a portion of said drive member extending through said opening.

6. The medication dispensing apparatus of claim 5 wherein distal movement of said drive member first part causes advancement of said piston in the same distance and direction, wherein said drive member first part comprises at least one longitudinally extending row of ratchet teeth and said drive member second part comprises a least one pawl that interfits with said at least one longitudinally extending row of ratchet teeth.

7. The medication dispensing apparatus of claim 6 further comprising at least one anti-back up member operably engaging said drive member first part to prevent movement of said drive member first part in a proximal direction within said housing.

8. The medication dispensing apparatus of claim 1 wherein said plunger comprises a first part, a second part, and a biasing element captured in a preloaded state to bias said first and second plunger parts apart, the preload of said preloaded state selected large enough to allow said plunger to properly operate the apparatus without further compression of said biasing element, and wherein said biasing element is compressible prior to apparatus damaging forces being transferred therethrough during initial shifting of said plunger from said proximal position toward said distal position.

9. The medication dispensing apparatus of claim 8 wherein said plunger first part comprises said rack in meshed engagement with said first pinion, wherein said plunger second part is manually pushable relative to said housing, and wherein said biasing element and said first and second plunger parts are selected and configured to allow said plunger second part to be shifted completely to said distal position from said proximal position without distal movement of said plunger first part and with compression of said biasing element.

10. The medication dispensing apparatus of claim 9 wherein said biasing element comprises a coiled spring having a first end that directly engages said plunger first part and a second end that directly engages said plunger second part.

11. The medication dispensing apparatus of claim 1 further comprising means for preventing an injection until the plunger has been manually shifted to said proximal position that corresponds to a fully cocked position.

12. The medication dispensing apparatus of claim 11 wherein said injection preventing means comprises a guide and a follower, said guide axially fixed within said housing and having a proximal end, a distal end, a first travel surface and a second travel surface, said first travel surface interrupted by a plurality of ratchet teeth, said follower comprising a pawl of said plunger, wherein said pawl slides along said first travel surface over said plurality of ratchet teeth during movement of said plunger from said distal position to said fully cocked position, whereby interaction of said ratchet teeth and said pawl limit distal travel of said plunger, and wherein said follower passes said second travel surface during movement of said plunger from said fully cocked position to said distal position.

13. The medication dispensing apparatus of claim 12 wherein said guide is integrally formed with said housing.

14. The medication dispensing apparatus of claim 12 wherein said guide proximal end cams said pawl to shift from said first travel surface to said second travel surface during movement of said plunger from said fully cocked position toward said distal position.

15. The medication dispensing apparatus of claim 12 wherein said pawl snaps against another element to provide an audible indication of the completion of pen cocking when said pawl passes said guide proximal end during movement of said plunger to said fully cocked position.

16. The medication dispensing apparatus of claim 1 wherein said first pinion and said second pinion are corotatable and coaxially arranged within said housing.

17. The medication dispensing apparatus of claim 1 wherein said second pinion comprises a pair of mirror image pinions that are coaxial with and flank said first pinion, and wherein said first and second pinions comprise a one-piece construction.

* * * * *